United States Patent [19]

Mackey et al.

[11] Patent Number: 5,952,043
[45] Date of Patent: *Sep. 14, 1999

[54] PROCESS FOR MAKING WET-LIKE CLEANING WIPES AND LIKE ARTICLES COMPRISING AN EMULSION HAVING A CONTINUOUS LIPID PHASE

[75] Inventors: Larry Neil Mackey, Fairfield; Arthur Wong, West Chester; Edward Aprahamian, Jr., Cincinnati; Gayle Marie Frankenbach, Cincinnati; Magda El-Nokaly, Cincinnati; Godfrey Reiter, Cincinnati; Paul Seiden, Cincinnati; John Michael Blevins, Cincinnati; John William Toussant, West Chester; Paul Dennis Trokhan, Hamilton, all of Ohio

[73] Assignee: The Procter & Gamble Company, Cincinnati, Ohio

[ * ] Notice: This patent is subject to a terminal disclaimer.

[21] Appl. No.: 09/139,860

[22] Filed: Aug. 25, 1998

Related U.S. Application Data

[60] Division of application No. 08/761,097, Dec. 5, 1996, Pat. No. 5,863,663, which is a continuation-in-part of application No. 08/336,456, Nov. 9, 1994, abandoned.

[51] Int. Cl.$^6$ .................................. B05D 1/00; B05D 5/00
[52] U.S. Cl. ................... 427/209; 424/70.12; 424/78.03; 424/402; 427/288; 427/374.1; 427/421
[58] Field of Search ..................................... 427/209, 288, 427/374.1, 421; 424/70.12, 78.03, 402

[56] References Cited

U.S. PATENT DOCUMENTS

| | | | |
|---|---|---|---|
| 2,868,824 | 1/1959 | Haluska | 260/448.2 |
| 3,215,707 | 11/1965 | Rense | 260/326.3 |
| 3,231,587 | 1/1966 | Rense | 260/346.8 |
| 3,818,533 | 6/1974 | Scheuer | 15/104.93 |
| 3,819,530 | 6/1974 | Ratledge et al. | 252/311.5 |
| 3,847,637 | 11/1974 | Luszczak | 106/271 |

(List continued on next page.)

FOREIGN PATENT DOCUMENTS

| | | | |
|---|---|---|---|
| 1 132 908 | 10/1982 | Canada | 167/310 |
| 0 110 678 A2 | 6/1984 | European Pat. Off. | C08K 7/00 |
| 0 259 034 A2 | 3/1988 | European Pat. Off. | A61K 7/00 |
| 0 365 160 | 9/1989 | European Pat. Off. | A61K 7/40 |
| 0 501 791 A3 | 9/1992 | European Pat. Off. | C08G 77/46 |
| 0 545 002 A1 | 6/1993 | European Pat. Off. | C08G 77/46 |
| 0 631 774 A1 | 1/1995 | European Pat. Off. | A61K 9/113 |
| 2 321 389 | 12/1976 | France | B32B 29/02 |
| 3341770 A1 | 5/1983 | Germany | A61K 9/06 |
| 155758 | 9/1981 | India | A61K 7/00 |
| 2/152920 | 6/1990 | Japan | A61K 7/50 |
| 3/168118 | 7/1991 | Japan | A47L 13/17 |
| 59144426 | 8/1994 | Japan . | |
| WO 94/02120 | 2/1994 | WIPO | A61K 9/113 |

OTHER PUBLICATIONS

"Dow Corning Q2–5200 Formulation Aid", Dow Corning Corporation (1990).

*Primary Examiner*—Michael Lusignan
*Attorney, Agent, or Firm*—Carl J. Roof; Edward J. Milbrada; Jacobus C. Rasser

[57] ABSTRACT

Wet-like cleaning wipes and similar articles that are particularly useful in removing perianal soils. These wipes comprise a carrier substrate such as tissue paper web and a emulsion applied to the substrate, wherein the emulsion comprises a continuous external lipid phase and a dispersed internal polar phase (e.g., water). The continuous external lipid phase of this emulsion is sufficiently brittle that it ruptures when subjected to low shear during use to release the dispersed internal polar phase.

20 Claims, 2 Drawing Sheets

U.S. PATENT DOCUMENTS

| | | | |
|---|---|---|---|
| 3,896,807 | 7/1975 | Buchalter | 128/261 |
| 3,919,149 | 11/1975 | Cushman et al. | 260/28.5 AV |
| 3,965,518 | 6/1976 | Muoio | 15/104.93 |
| 3,982,993 | 9/1976 | Fife | 162/158 |
| 4,043,829 | 8/1977 | Ratledge et al. | 106/271 |
| 4,082,887 | 4/1978 | Coates | 428/289 |
| 4,104,403 | 8/1978 | Barker et al. | 424/365 |
| 4,112,167 | 9/1978 | Dake et al. | 428/154 |
| 4,117,199 | 9/1978 | Gotoh et al. | 428/486 |
| 4,122,029 | 10/1978 | Gee et al. | 252/309 |
| 4,137,358 | 1/1979 | Hartz | 428/272 |
| 4,203,877 | 5/1980 | Baker | 260/18 |
| 4,246,423 | 1/1981 | Martin | 556/423 |
| 4,293,611 | 10/1981 | Martin | 428/266 |
| 4,339,276 | 7/1982 | Yokoyama et al. | 106/271 |
| 4,377,649 | 3/1983 | Sweeney et al. | 524/49 |
| 4,381,241 | 4/1983 | Romenesko et al. | 252/8.5 P |
| 4,385,049 | 5/1983 | Cuca | 424/167 |
| 4,421,656 | 12/1983 | Donatelli et al. | 252/8.5 P |
| 4,446,051 | 5/1984 | Berthod et al. | 252/309 |
| 4,468,254 | 8/1984 | Yokoyama et al. | 106/271 |
| 4,481,243 | 11/1984 | Allen | 428/154 |
| 4,513,051 | 4/1985 | Lavash | 428/212 |
| 4,514,345 | 4/1985 | Johnson et al. | 264/22 |
| 4,520,160 | 5/1985 | Brown | 524/765 |
| 4,606,913 | 8/1986 | Aronson et al. | 424/59 |
| 4,698,178 | 10/1987 | Hüttinger et al. | 252/309 |
| 4,708,753 | 11/1987 | Forsberg | 149/2 |
| 4,782,095 | 11/1988 | Gum | 514/937 |
| 4,801,447 | 1/1989 | Gum | 424/68 |
| 4,844,756 | 7/1989 | Forsberg | 149/2 |
| 4,853,474 | 8/1989 | Bahr et al. | 556/445 |
| 4,875,927 | 10/1989 | Tadros | 71/94 |
| 5,021,405 | 6/1991 | Klimisch | 514/63 |
| 5,047,175 | 9/1991 | Forsberg | 252/356 |
| 5,133,972 | 7/1992 | Ferrini et al. | 424/449 |
| 5,136,068 | 8/1992 | Bahr et al. | 556/445 |
| 5,162,378 | 11/1992 | Guthauser | 514/785 |
| 5,210,102 | 5/1993 | Klimisch | 514/784 |
| 5,245,025 | 9/1993 | Trokhan et al. | 536/56 |
| 5,247,044 | 9/1993 | Crivello et al. | 528/15 |
| 5,277,761 | 1/1994 | Van Phan et al. | 162/109 |
| 5,292,503 | 3/1994 | Raleigh et al. | 424/59 |
| 5,362,482 | 11/1994 | Yoneyama et al. | 424/69 |
| 5,378,455 | 1/1995 | Kealey et al. | 424/73 |
| 5,387,417 | 2/1995 | Rentsch | 424/401 |
| 5,470,551 | 11/1995 | Dubief et al. | 424/70.12 |
| 5,482,703 | 1/1996 | Pings | 424/70.12 |
| 5,503,715 | 4/1996 | Trokhan et al. | 162/296 |
| 5,525,345 | 6/1996 | Warner et al. | 424/402 |
| 5,534,326 | 7/1996 | Trokhan et al. | 428/131 |
| 5,756,112 | 5/1998 | Mackey | 424/402 |
| 5,763,332 | 6/1998 | Gordon et al. | 442/84 |
| 5,863,663 | 1/1999 | Mackey et al. | |

PROCESS FOR MAKING WET-LIKE CLEANING WIPES AND LIKE ARTICLES COMPRISING AN EMULSION HAVING A CONTINUOUS LIPID PHASE

CROSS REFERENCE TO RELATED APPLICATION

This application is a divisional application of U.S. patent application Ser. No. 08/761,097, filed Dec. 5, 1996, now U.S. Pat. No. 5,863,663, patented Jan. 26, 1998, which is a continuation-in-part application of U.S. patent application Ser. No. 08/336,456, filed Nov. 9, 1994 by L. N. Mackey et al. (now abandoned).

TECHNICAL FIELD

This application relates to articles that are useful in cleansing and especially in removing perianal soils. This application particularly relates to wet-like cleaning wipes made from carrier substrates treated with a high internal phase inverse emulsion.

BACKGROUND OF THE INVENTION

Cleansing the skin is a personal hygiene problem not always easily solved. Of course, the common procedure of washing the skin with soap and water works well, but at times may be either unavailable or inconvenient to use. While soap and water could be used to clean the perianal region after defecation for example, such a procedure would be extremely burdensome. Dry tissue products are therefore the most commonly used post-defecation anal cleansing product. These dry tissue products are usually referred to as "toilet tissue" or "toilet paper."

The perianal skin is marked by the presence of fine folds and wrinkles (sulci) and by hair follicles which make the perianal region one of the more difficult anatomical areas to cleanse. During defecation, fecal matter is excreted through the anus and tends to accumulate in hard to reach locations such as around the base of hairs and in the sulci of the skin's surface. As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult.

Failure to remove fecal matter from the anal area can have a deleterious effect on personal hygiene. The fecal matter remaining on the skin after post-defecation cleansing has a high bacterial and viral content, is malodorous and is generally dehydrated. These characteristics increase the likelihood of perianal disorders and cause personal discomfort (e.g., itching, irritation, chafing, etc.). Further, the residual fecal matter stains undergarments and causes unpleasant odors to emanate from the anal region. Thus, the consequences of inadequate perianal cleansing are clearly unattractive.

For those individuals suffering from anal disorders such as pruritis ani, hemorrhoids, fissures, cryptitis, or the like, the importance of adequate perianal cleansing takes on heightened significance. Perianal disorders are usually characterized by openings in the skin through which the bacteria and viruses in the residual fecal matter can readily enter. Those people afflicted with anal disorders must, therefore, achieve a high degree of perianal cleansing after defecation or risk the likely result that their disorders will be aggravated by the bacteria and viruses remaining on the skin.

At the same time anal disorder sufferers face more severe consequences from insufficient post defecation cleaning, they have greater difficulty in achieving a satisfactory level of soil removal. Anal disorders generally render the perianal region extremely sensitive and attempts to remove fecal matter from this region by wiping with even normal wiping pressure causes pain and can further irritate the skin. Attempts to improve soil removal by increasing the wiping pressure can result in intense pain. Conversely, attempts to minimize discomfort by reducing the wiping pressure result in an increased amount of residual fecal matter left on the skin.

Conventional toilet tissue products used for anal cleaning are essentially dry, low density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil-soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, causing it to adhere more tenaciously to the perianal skin and hair and making its removal difficult in the extreme. Pressing the tissue forcefully against the perianal skin will remove more of the fecal matter but is intensely pail for people suffering from anal disorders and can excoriate even normal perianal skin, potentially causing irritation, inflammation, pain, bleeding, and infection.

To improve perianal cleaning, wipes have been developed that are kept in some sort of dispenser and are typically soaked in a reservoir of a moistening solution. Examples of such products include wipes that are often used to clean babies after bowel movements and can have other additives in the moistening solution to soothe the skin. These wipes can have permanent wet strength such that they are not flushable. Also, these prior wipes are often too wet to dry the skin and tend to have a "cold" feel. There is also a lack of consistency in terms of the moisture content of each of the wipes.

Moistenable dry tissue products have also been used in perianal cleaning. These moistenable tissue products usually have temporary wet strength such that they are flushable. However, the users of these products have to wet the tissue which can be inconvenient. It is also difficult to get appropriate moisture levels on such products. Also, the temporary wet strength of such products is typically inadequate and needs to be improved.

Accordingly, it would be desirable to provide products for perianal cleaning that: (1) have consistent levels of moistening solution; (2) can have adequate temporary wet strength so as to be flushable; (3) have an adequate, consistent moisture level to provide effective cleaning; and (4) remain essentially dry until used for cleaning purposes.

DISCLOSURE OF THE INVENTION

The present invention relates to articles useful in cleansing, and particularly wet-like cleansing wipes that are especially useful in removing perianal soils. These articles comprise:

a. a carrier, b. an emulsion applied to the carrier, the emulsion comprising:

(1) from about 2 to about 60% of a continuous solidified external lipid phase comprising a waxy lipid material having a melting point of about 30° C. or higher,
(2) from about 39 to about 97% of an internal polar phase dispersed in the external lipid phase; and
(3) an effective amount of an emulsifier capable of forming the emulsion when the external lipid phase is in a fluid state.

The present invention further relates to a method for making these articles. This method comprises the steps of:
A. forming an emulsion comprising:
   (1) from about 2 to about 60% of a continuous external lipid phase comprising a waxy lipid material having a melting point of about 30° C or higher;
   (2) from about 39 to about 97% of an internal polar phase dispersed in the external lipid phase; and
   (3) an effective amount of an emulsifier capable of forming the emulsion when the external lipid phase is in a fluid state;
B. applying the emulsion to a carrier at a temperature sufficiently high such that the external lipid phase has a fluid or plastic consistency;
C. cooling the applied emulsion to a temperature sufficiently low such that the external lipid phase solidifies.

These articles have a number of significant advantages over prior cleaning products, especially when in the form of wet-like cleansing wipes used to remove perianal soils. These articles release significant quantities of the internal polar phase (e.g., water) during use for comfortable, more effective cleaning. The continuous lipid phase of the emulsion is sufficiently brittle so as to be easily disrupted by low shear contact (e.g., during the wiping of the skin) to readily release this internal phase, but sufficiently tough to avoid premature release of the internal phase during the rigors of processing. The continuous lipid phase of these articles is also sufficiently stable during storage so as to prevent significant evaporation of the internal polar phase. The normal tensile strength and flushability properties of these articles are not adversely affected when treated with the high internal phase inverse emulsions of the present invention. As a result, users of these articles get comfortable, efficient, moist cleaning without having to change their normal cleaning habits.

Besides perianal cleaning, these articles can be used in many other applications requiring the delivery of an internal polar liquid phase such as water, as well as actives that are dispersible in such polar materials. These include hard surface cleaning of floors, countertops, sinks, bathtubs, toilets, and the like, as well as the delivery of antimicrobial or pharmaceutical actives that are soluble or dispersible in polar liquids. These articles can also perform multiple functions. For example, the high internal phase inverse emulsion applied to these articles can be formulated to provide cleaning and waxing benefits at the same time when used on items such as furniture, shoes, automobiles, and the like.

DETAILED DESCRIPTION OF THE INVENTION

Figure 1:
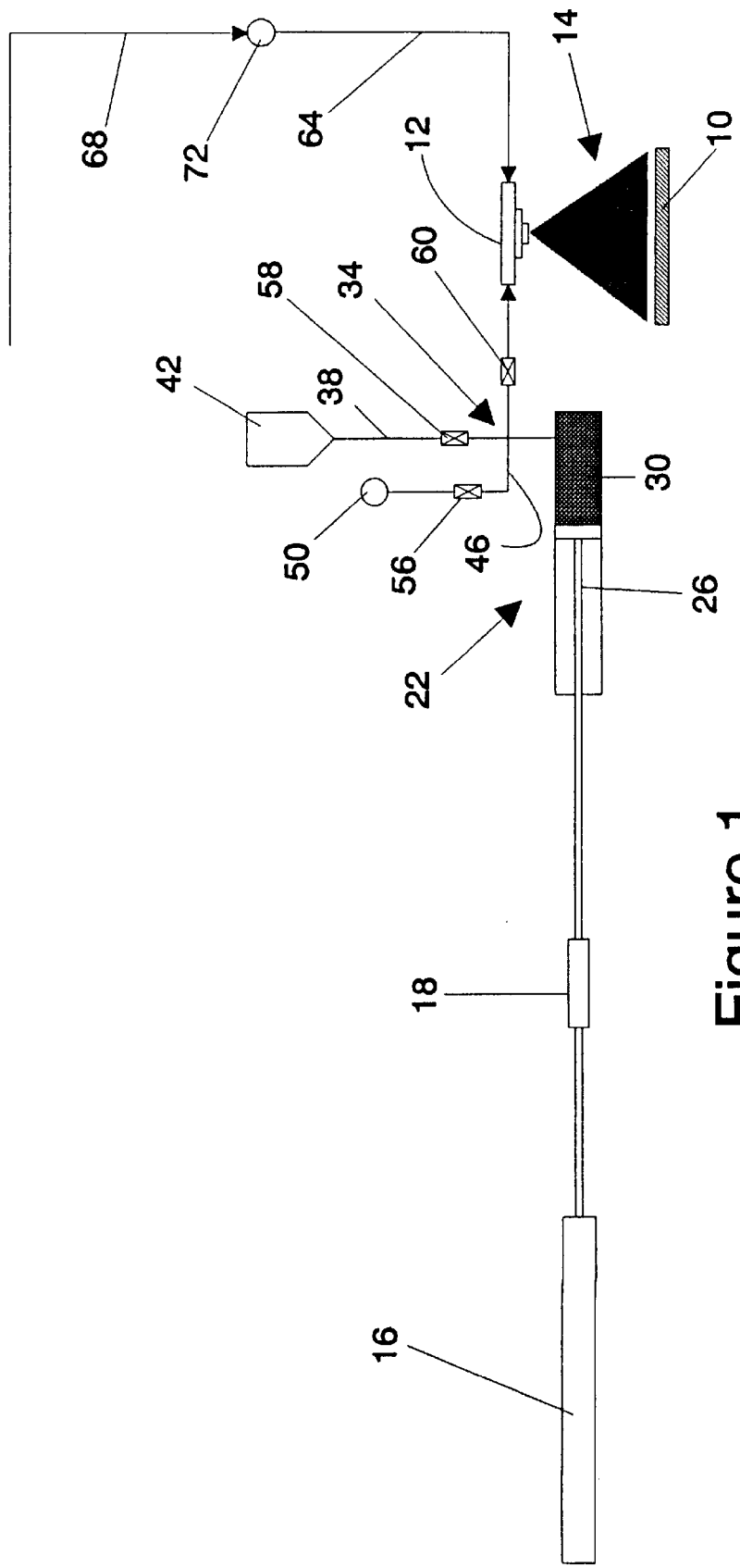
FIG. 1 is a schematic representation illustrating a spray system for applying the high internal phase inverse emulsions of the present invention to a carrier substrate such as a paper web.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the terms "detergent", "detersive surfactant" and "detergent surfactant" are used interchangeably, and refer to any substance that reduces the surface tension of water, specifically a surface-active agent which concentrates at oil-water interfaces, exerts emulsifying action, and thus aids in removing soils.

As used herein, the term "polar" refers to a molecule that possesses a dipole moment, i.e., a molecule of which the positive and negative electrical charges are permanently separated, as opposed to a nonpolar molecule in which the charges coincide. A "polar fluid" is a fluid comprising one or more polar constituents.

All percentages, ratios and proportions used herein are by weight unless otherwise specified.

A. Carriers for High Internal Phase Inverse Emulsion

Carriers useful in the present invention can be in variety of substrate forms. Suitable carrier substrates include woven materials, nonwoven materials, foams, sponges, battings, balls, puffs, films, and the like. Particularly preferred substrates for use in the present invention are nonwoven types. These nonwoven substrates can comprise any conventionally fashioned nonwoven sheet or web having suitable basis weight, caliper (thickness), absorbency and strength characteristics. Nonwoven substrates can be generally defined as bonded fibrous or filamentous products having a web structure, in which the fibers or filaments are distributed randomly as in "air-laying" or certain "wet-laying" processes, or with a degree of orientation, as in certain "wet-laying" or "carding" processes. The fibers or filaments of such nonwoven substrates can be natural (e.g., wood pulp, wool, silk, jute, hemp, cotton, linen, sisal or ramie) or synthetic (e.g., rayon, cellulose ester, polyvinyl derivatives, polyolefins, polyamides or polyesters) and can be bonded together with a polymeric binder resin. Examples of suitable commercially available nonwoven substrates include those marketed under the tradename Sontara® by DuPont and Polyweb® by James River Corp.

For reasons of cost, ease of manufacture and article disposability (e.g., flushability), the preferred type of nonwoven substrate used in wipes of the present invention comprise those made from wood pulp fibers, i.e., paper webs. As noted, paper webs can be prepared by either air-laying or wet-laying techniques. Air-laid paper webs such as Air Tex® SC130 are commercially available from James River Corp.

More conventionally, paper webs are made by wet-laying procedures. In such procedures, a web is made by forming an aqueous papermaking furnish, depositing this furnish onto a foraminous surface, such as a Fourdrinier wire, and by then removing water from the furnish, for example by gravity, by vacuum assisted drying and/or by evaporation, with or without pressing, to thereby form a paper web of desired fiber consistency. In many cases, the papermaking apparatus is set up to rearrange the fibers in the slurry of papermaking furnish as dewatering proceeds in order to form paper substrates of especially desirable strength, hand, bulk, appearance, absorbency, etc.

The papermaking furnish utilized to form the preferred paper web substrates for articles of the present invention essentially comprises an aqueous slurry of papermaking fibers (i.e., paper pulp) and can optionally contain a wide variety of chemicals such as wet strength resins, surfactants, pH control agents, softness additives, debonding agents and the like. Wood pulp in all its variations can be used to form the papermaking furnish. Wood pulps useful herein include both sulfite and sulfate pulps, as well as mechanical, thermomechanical and chemi-thermo-mechanical pulps, all of which are well known to those skilled in the papermaking art. Pulps derived from both deciduous or coniferous trees can be used. Preferably the papermaking furnish used to form the preferred paper web substrates for wipes of the present invention comprises Kraft pulp derived from northern softwoods.

A number of papermaking processes have been developed which utilize a papermaking apparatus that forms paper webs having particularly useful or desirable fiber configurations. Such configurations can serve to impart such characteristics of the paper web as enhanced bulk, absorbency and strength. One such process employs an imprinting fabric in the papermaking process that serves to impart a knuckle pattern of high density and low density zones into the resulting paper web. A process of this type, and the papermaking apparatus for carrying out this process, is described in greater detail in U.S. Pat. No. 3,301,746 (Sanford et al), issued Jan. 31, 1967, which is incorporated by reference.

Another papermaking process carried out with a special papermaking apparatus, is one that provides a paper web having a distinct, continuous network region formed by a plurality of "domes" dispersed throughout the network region on the substrate. Such domes are formed by compressing an embryonic web as formed during the papermaking process into a foraminous deflection member having a patterned network surface formed by a plurality of discrete isolated deflection conduits in the deflection member surface. A process of this type, and apparatus for carrying out such a process, is described in greater detail in U.S. Pat. No. 4,529,480 (Trokhan), issued Jul. 16, 1985; U.S. Pat. No. 4,637,859 (Trokhan), issued Jan. 20, 1987; and; U.S. Pat. No. 5,073,235 (Trokhan), issued Dec. 17, 1991, all of which are incorporated by reference. Another type of papermaking process, and apparatus to carry it out that is suitable for making layered composite paper substrates is described in U.S. Pat. No. 3,994,771 (Morgan et al); issued Nov. 30, 1976, which is incorporated by reference.

The preferred paper web substrates can form one of two or more plies that can be laminated together. Lamination, and lamination carried out in combination with an embossing procedure to form a plurality of protuberances in the laminated product, is described in greater detail in U.S. Pat. No. 3,414,459 (Wells); issued Dec. 3, 1968, which is incorporated by reference. These paper substrates preferably have a basis weight of between about 10 g;/m$^2$ and about 65 g/m$^2$, and density of about 0.6 g/cc or less. More preferably, the basis weight will be about 40 g/m$^2$ or less and the density will be about 0.3 g/cc or less. Most preferably, the density will be between about 0.04 g/cc and about 0.2 g/cc. See Column 13, lines 61–67, of U.S. Pat. No. 5,059,282 (Ampulski et al), issued Oct. 22, 1991, which describes how the density of tissue paper is measured. (Unless otherwise specified, all amounts and weights relative to the paper web substrates are on a dry basis.)

In addition to papermaking fibers, the papermaking furnish used to make these paper web substrate can have other components or materials added thereto as can be or later become known in the art. The type of additives desirable will be dependent upon the particular end use of the tissue sheet contemplated. For example, in wipe products such as toilet paper, paper towels, facial tissues, baby wipes and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins that have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmigton Del., which markets such resins under the mark Kymene® 557H.

Polyacrylamide resins have also been found to be of utility as wet strength resins. These resins are described in U.S. Pat. No. 3,556,932 (Coscia et al), issued Jan. 19, 1971, and U.S. Pat. No. 3,556,933 (Williams et al), issued Jan. 19, 1971, both of which are incorporated by reference. One commercial source of polyacrylamide resins is American Cyananid Co. of Stamford, Conn., which markets one such resin under the mark Parez® 631 NC.

Still other water-soluble cationic resins finding utility wet strength resins are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10 (manufactured by Japan Carlit), CoBond 1000 (manufactured by National Starch and Chemical Company), and Parez 750 (manufactured by American Cyanamide Co.) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the paper substrate, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the paper substrate.

In general, suitable starch binders for these paper web substrates are characterized by water solubility, and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn," H. H. Schopmeyer, Food Industries, December 1945, pp.106–108 ;(Vol. pp.1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

B. Composition of High Internal Phase Inverse Emulsion

The articles of the present invention comprise an emulsion that is applied to the carrier substrate. This emulsion comprises: (1) a continuous solidified lipid phase; (2) an emulsifier that forms the emulsion when the lipid phase is fluid; and (3) an internal polar phase dispersed in the lipid phase. Because the internal phase contains a high level of one or more polar liquids, this emulsion is typically referred to as a "high internal phase inverse emulsion". This high internal phase inverse emulsion ruptures when subjected to low shear during use, e.g., wiping of the skin or other surface, so as to release the internal polar phase.

The continuous solidified lipid phase provides the essential stabilizing structure for the high internal phase inverse emulsions of the present invention. In particular, this continuous lipid phase is what keeps the dispersed internal polar phase from being prematurely released prior to use of the article, such as during the rigors of processing.

The continuous lipid phase can comprise from about 2 to about 60% of the emulsion of the present invention. Preferably, this continuous lipid phase will comprise from about 5 to about 30% of the emulsion. Most preferably, this lipid phase will comprise from about 6 to about 15% of the emulsion.

The major constituent of this continuous lipid phase is a waxy lipid material. This lipid material is characterized by a melting point of about 30° C. or higher, i.e., is solid at ambient temperatures. Preferably, this lipid material has a melting point of about 50° C. or higher. Typically, this lipid material has a melting point in the range of from about 40° to about 80° C., more typically in the range of from about 60° to about 70° C.

Although this waxy lipid material is solid at ambient temperatures, it also needs to be fluid or plastic at those temperatures at which the high internal phase inverse emulsion is applied to the carrier substrate. Moreover, even though this lipid material is fluid or plastic at those temperatures at which the emulsion is applied to the carrier substrate, it should still desirably be somewhat stable (i.e., unmelted) for extended periods of time at elevated temperatures (e.g., about 50° C. or higher) that are normally encountered during storage and distribution of the articles of the present invention. This lipid material also needs to be sufficiently brittle at the shear conditions of use of the article such that it ruptures and releases the dispersed internal polar phase. These lipid materials should also desirably provide a good feel to the skin when used in personal care products such as wet-like cleansing wipes used in perianal cleaning.

Suitable waxy lipid materials for use in the high internal phase inverse emulsion of the present invention include natural and synthetic waxes, as well as other oil soluble materials having a waxy consistency. As used herein, the term "waxes" refers to organic mixtures or compounds that are generally water-insoluble and tend to exist as amorphous or microcrystalline solids at ambient temperatures (e.g., at about 25° C). Suitable waxes include various types of hydrocarbons, as well as esters of certain fatty acids (e.g., saturated triglycerides) and fatty alcohols. They can be derived from natural sources (i.e., animal, vegetable or mineral) or can be synthesized. Mixtures of these various waxes can also be used.

Some representative animal and vegetable waxes that can be used in the present invention include beeswax, carnauba, spermaceti, lanolin, shellac wax, candelilla, and the like. Particularly preferred animal and vegetable waxes are beeswax, lanolin and candelilla. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Particularly preferred mineral waxes are petrolatum, microcrystalline wax, yellow ceresine wax, and white ozokerite wax. Representative synthetic waxes that can be used in the present invention include ethylenic polymers such as polyethylene wax, chlorinated naphthalenes such as "Halowax," hydrocarbon type waxes made by Fischer-Tropsch synthesis, and the like. Particularly preferred synthetic waxes are polyethylene waxes.

Besides the waxy lipid material, the continuous lipid phase can include minor amounts of other lipophilic or lipid-miscible materials. These other lipophilic/lipid-miscible materials are typically included for the purpose of stabilizing the emulsion to minimize loss of the internal polar phase or improving the aesthetic feel of the emulsion on the skin. Suitable materials of this type that can be present in the continuous lipid phase include hot melt adhesives such as Findley 193-336 resin, long chain alcohols such as cetyl alcohol, steiaryl alcohol, and cetaryl alcohol, water-insoluble soaps such as aluminum stearate, silicone polymers such as polydimethylsiloxanes, hydrophobically modified silicone polymers such as phenyl trimethicone, and the like. Other suitable lipophilic/lipid miscible materials include polyol polyesters. By "polyol polyester" is meant a polyol having at least 4 ester groups. By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols and other sugar derivatives (e.g., alkyl glycosides), polyglycerols (e.g., diglycerol and triglycerol), pentaerythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol. With respect to the polyol polyesters useful herein, it is not necessary that all of the hydroxyl groups of the polyol be esterified, however disaccharides polyesters should have no more than 3, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

By "liquid polyol polyester" is meant a polyol polyester from the hereinbefore described groups having a fluid consistency at or below about 37° C. By "solid polyol polyester" is meant a polyol polyester from the hereinbefore described groups having a plastic or solid consistency at or above about 37° C. Liquid polyol polyesters and solid polyol polyesters may be successfully employed as emollients and immobilizing agents, respectively, in emulsions of the present invention. In some cases, solid polyol polyesters may also provide some emolliency functionality.

Typically, the major component of the high internal phase inverse emulsions of the present invention is the dispersed internal polar phase. This internal phase can provide a number of different benefits when released. In preferred emodiments, the polar phase will contain a significant percentage of water. For example, in preferred wet-like cleaning wipes for perianal cleaning, the internal polar phase will comprise a significant level of water; this released internal water phase that provides the primary cleansing action for these wipes. In these preferred emodiments, the polar phase will contain a significant percentage of water, preferably at least about 60%, by weight of the internal polar phase, more preferably at least about 75%, by weight, still more preferably at least about 85%, by weight.

The internal polar phase can comprise from about 39 to about 97% of the emulsion of the present invention. Preferably, this internal polar phase will comprise from about 67 to about 92% of the emulsion. Most preferably, this polar phase will comprise from about 82 to about 91% of the emulsion.

In preferred embodiments, where the internal phase comprises significant amounts of water, this internal polar phase can comprise other water-soluble or dispersible materials that do not adversely affect the stability of the high internal phase inverse emulsion. One such material that is typically included in the internal water phase is a water-soluble electrolyte. The dissolved electrolyte minimizes the tendency of materials present in the lipid phase to also dissolve in the water phase. Any electrolyte capable of imparting ionic strength to the water phase can be used. Suitable electrolytes include the water soluble mono-, di-, or trivalent inorganic salts such as the water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about I to about 20% of the water phase.

Other water-soluble or dispersible materials that can be present in the internal water phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the water phase.

Other water-soluble or dispersible materials that can be present in the internal water phase include polycationic polymers to provide steric stabilization at the water-lipid interface and nonionic polymers that also stabilize the water-in-lipid emulsion. Suitable polycationic polymers include Reten 201, Kymene® 557H and Acco 711. Suitable nonionic polymers include polyethylene glycols (PEG) such as Carbowax. These polycationic and nonionic polymers will typically be included in a concentration in the range of from about 0.1 to about 1.0% of the water phase.

In addition or alternative to containing water, the internal polar phase may comprise polar materials, including solvents such as ethanol, isopropanol, butanol and hexanol; glycols or substituted glycols such as propylene glycol, butylene glycol, 2,2,4-trimethylpentane-1,3-diol or hexylene glycol; polyglycols such as diethylene glycol or triethylene glycol; glycol ethers such as short chain (e.g., $C_1$–$C_6$) derivatives of oxyethylene glygol and oxypropylene glycol, such as mono- and di-ethylene glycol n-hexyl ether, mono-, di- and tri-propylene glycol n-butyl ether; and the like. Also, solvents such as tetrahydrofuran, dimethyl sulfoxide, acetone and the like may be included in the internal polar phase.

Another key component of the high internal phase inverse emulsion of the present invention is an emulsifier. In the emulsions of the present invention, the emulsifier is included in an effective amount. What constitutes an "effective amount" will depend on a number of factors including the respective amounts of the lipid and internal polar phase components, the type of emulsifier used, the level of impurities present in the emulsifier, and like factors. Typically, the emulsifier comprises from about 1 to about 10% of the emulsion. Preferably, this emulsifier will comprise from about 3 to about 6% of the emulsion. Most preferably, this emulsifier will comprise from about 4 to about 5% of the emulsion.

This emulsifier needs to be substantially lipid-soluble or miscible with the lipid phase materials, especially at the temperatures at which the lipid material melts. It also should have a relatively low HLB value. Emulsifiers suitable for use in the present invention have HLB values typically in the range of from about 2 to about 5 and can include mixtures of different emulsifiers. Preferably, these emulsifiers will have HLB values in the range of from about 2.5 to about 3.5.

Emulsifiers suitable for use in the present invention include certain sorbitan esters, preferably the sorbitan esters of $C_{16}$–$C_{22}$ saturated, unsaturated or branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65) and sorbitan dipalmitates (e.g., SPAN® 40). Sorbitan monoisostearate and sorbitan sesquioleate are particularly preferred emulsifiers for use in the present invention.

Other suitable emulsifiers for use in the present invention include certain glyceryl monoesters, preferably glyceryl monoesters of $C_{16}$–$C_{22}$ saturated, unsaturated or branched chain fatty acids such as glyceryl monosterate, glyceryl monopalmitate, and glyceryl monobehenate; certain sucrose fatty acid esters, preferably sucrose esters of the $C_{12}$–$C_{22}$ saturated, unsaturated, and branched chain fatty acids such as sucrose trilaurate and sucrose distearate (e.g., Crodesta® F10), and certain polyglycerol esters of $C_{16}$–$C_{22}$ saturated, unsaturated or branched fatty acids such as diglycerol monooleate and tetraglycerol monooleate. In addition to these primary emulsifiers, coemulsifiers can be used to provide additional emulsion stability. Suitable coemulsifiers include phosphatidyl cholines and phosphatidyl choline-containing compositions such as the lecithins; long chain $C_{16}$–$C_{22}$ fatty acid salts such as sodium stearate; amine polymers such as polyethylene amine and ethoxylated polyethylene amine; long chain $C_{16}$–$C_{22}$ dialiphatic, short chain $C_1$–$C_4$ dialiphatic quaternary ammonium salts such as ditallow dimethyl ammonium chloride and ditallow dimethyl ammonium methylsulfate; long chain $C_{16}$–$C_{22}$ dialkoyl (alkenoyl)-2-hydroxyethyl, short chain $C_1$–$C_4$ dialiphatic quaternary ammonium salts such as ditallowoyl-2-hydroxyethyl dimethyl ammonium chloride, the long chain $C_{16}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain $C_1$–$C_4$ dialiphatic, long chain $C_{16}$–$C_{22}$ monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries). Interfacial tension modifiers, such as common nonionic surfactants (e.g., neodal, pluronics) and cetyl and stearyl alcohol, for closer packing at the polar internal phase-lipid external phase interface can also be included.

The high internal phase inverse emulsions of the present invention can also comprise other optional components typically present in moisture containing solutions of this type. These optional components can be present in either the continuous lipid phase or the internal polar phase and include perfumes, antimicrobial (e.g., antibacterial) actives, pharmaceutical actives, deodorants, opacifiers, astringents, skin conditioners, cosmetics, cleansers, surface conditioners, insect repellants, pH buffers, and the like, as well as mixtures of these components. All of these materials are well known in the art as additives for such formulations and can be employed in effective, appropriate amounts in the emulsions of the present invention. A particularly preferred optional component that is included the emulsions of wet-like cleansing wipes according to the present invention is glycerin as a skin conditioning agent.

The emulsion component of the articles of the present invention is described and claimed herein in terms of components (i.e., lipid phase components, internal polar phase components, emulsifier components, etc.), and corresponding amounts of these components, that are present after emulsion formation. That is, when the stable emulsion is formed and applied to the carrier. It is understood, however, that the description (components and amounts) of the emulsion also encompasses emulsions formed by combining the described components at the described levels, regardless of the chemical identity of the components after emulsification and application to the carrier.

C. Other Optional Wipe Components

Besides the high internal phase inverse emulsion, there are other optional components that can be included in the articles of the present invention, typically for the purpose of improving the cleaning performance of the article when the internal polar phase of the emulsion is released. Certain of these optional components cannot be present in the emulsion at significant levels (e.g., greater than 2% of the internal polar phase) because they can cause premature disruption of the emulsion. These include various anionic detergent surfactants that have relatively high HLB values (e.g., HLBs of from about 10 to about 25), such as sodium linear alkylbenzene sulfonates (LAS) or alkyl ethoxy sulfates (AES), as well as nonionic detergent surfactants such as alkyl ethoxylates, alkyl amine oxides, alkyl polyglycosides, zwitterionic detergent surfactants, ampholytic detergent surfactants, and cationic detergent surfactants such as cetyl trimethyl ammonium salts, and lauryl trimethyl ammonium salts. See U.S. Pat. No. 4,597,898 (Vander Meer), issued Jul. 1, 1986 (herein incorporated by reference), especially columns 12 through 16 for representative anionic, nonionic, zwitterionic, ampholytic and cationic detergent surfactants. Instead, these high HLB detergent surfactants can be applied or included in the article separately from the emulsion. For example, an aqueous solution of these high HLB detergent surfactants can be applied to one side of the carrier substrate, with the high internal phase inverse emulsion being applied to the other side of the substrate. During wiping, the emulsion is disrupted, releasing the internal polar phase (e.g., water) so that it can then be combined with the high HLB detergent surfactant to provide improved hard surface cleaning.

Though the description of the invention generally relates to applying a single emulsion to the carrier, it is recognized that two or more different emulsions may be utilized in preparing a single article. In such embodiments, the emulsions may differ in a variety of ways, including but not limited to the ratio of the internal polar phase and the external lipid phase, the emulsifiers used, the components used for either or both of the internal and lipid phases, and the like. Utilization of multiple emulsions in one article may be particulalry desirable when two or more components are incompatible with each other, but can each be included in separate emulsions. Alternatively, if a particular reaction is desired at the time of use, the reactants can be provided in separate emulsions. Upon shearing of the emulsions during use, the desired reaction will occur. For example, where foaming is desired during the wiping processes, a mild acid can be incorporated in the internal polar phase of one emulsion, while bicarbonate is incorporated in the internal polar phase of a second emulsion. Upon shearing of the emulsions during use, the reactants interact to provide the desired foam.

D. Preparation of Emulsion Treated Articles

In preparing the articles according to the present invention, the high internal phase inverse emulsion is initially formulated. Typically, this is achieved by blending or melting together the lipid phase components and the emulsifier. The particular temperature to which this lipid/emulsifier mixture is heated will depend on the melting point of the lipid phase components. Typically, this lipid/emulsifier mixture is heated to a temperature in the range from about 60° to about 90° C., preferably from about 70° to about 80° C., prior to being mixed, blended or otherwise combined with the polar phase components. The melted lipid/emulsifier mixture is then blended with the polar internal phase components and then mixed together, typically under low shear conditions to provide the emulsion.

This high internal phase inverse emulsion is then applied in a fluid or plastic state at the temperatures indicated above to the carrier substrate, e.g., a paper web. Any of a variety of methods that apply materials having a fluid or plastic consistency can be used to apply this emulsion. Suitable methods include spraying, printing (e.g., flexographic or screen printing), coating (e.g., gravure coating), extrusion, or combinations of these application techniques, e.g. spraying the detergent surfactant on the paper web, followed by gravure coating of the emulsion on the detergent treated web.

The emulsion can be applied either to one side or both sides of the paper web, or, in the case of multi-ply webs, can be applied to the inner surface(s) of the plies. For example, in the case of a two ply paper web, the emulsion can be applied to at least one of the opposed inner surfaces of the plies, leaving the outside surfaces of the paper web free of the emulsion. Typically, the emulsion is applied to both sides of the paper web. The application of the emulsion to both sides of the web can be either sequentially or simultaneously. Once the emulsion has been applied to the paper web, it is allowed to cool and solidify to form a solidified, typically discontinuous coating or film on the surface of the web.

The high internal phase inverse emulsion is typically applied to the paper web after the web has been dried, i.e. a "dry web" addition method. The emulsion can also be applied nonuniformly to the surface(s) of the web. By "nonuniform" is meant that the amount, pattern of distribution, etc. of the emulsion can vary over the surface of the paper web. For example, some portions of the surface of the paper web can have greater or lesser amounts of the emulsion, including portions of the surf that do not have any emulsion on it.

The high internal phase inverse emulsion can be applied to the paper web at any point after it has been dried. For example, the emulsion can be applied to the paper web after it has been creped from a Yankee dryer. Usually, it is preferred to apply the emulsion to the paper web as it is being unwound from a parent roll and prior to being wound up on smaller, finished product rolls.

In applying high internal phase inverse emulsions of the present invention to paper webs, spray and gravure coating methods are usually preferred. FIG. 1 illustrates one such preferred method where the emulsion is sprayed onto a paper web 10. Referring to FIG. 1, this spray system has a spray head 12 that applies a dispersed spray 14 of the emulsion onto web 10.

This spray system is actuated by an assembly that consists of a ball screw drive 16 that is connected by coupling 18 to a piston 26 of hydraulic cylinder 22. A portion of cylinder 22 is shown in FIG. 1 as being filled with the high internal phase inverse emulsion as indicated by 30. Cylinder 22 is heated to keep emulsion 30 in a fluid or plastic state. Emulsion 30 enters cylinder 22 via a 4-way coupling 34 that has a line 38 connected to a heated filling port 42. Coupling 34 also has a line 46 that is connected to pressure gauge 50 and spray head 12. There are three valves indicated as 56, 58 and 60 that control the flow of the emulsion in lines 38 and 46. The spray system shown in FIG. 1 also has a line 64 connected to spray head 12 that allows air indicated generally as 68 to be admitted to the spray head. Line 64 also has a pressure gauge and regulator 72 for controlling and measuring the air pressure in line. Lines 64 and 46 are heated to maintain the emulsion in a molten state prior to application to the web.

To fill cylinder 22 with emulsion 30, valves 56 and 60 are closed and valve 58 is opened. Ball screw drive 16 is actuated so that piston 26 moves to the left. The vacuum created in cylinder 22 draws the emulsion from filling port 46 through line 38 and into cylinder 22. To provide emulsion from cylinder 22 to spray head 12, valve 58 is closed and valves 56 and 60 are opened. The ball screw drive 16 is actuated so that piston 26 moves to the right. This forces emulsion 30 out of cylinder 22 and into line 46 of coupling 34. The emulsion then passes through valve 60 and into the spray head 12 where it is dispersed by incorporation of air from line 64 to provide dispersed spray 14 that is then applied to web 10.

Figure 2:
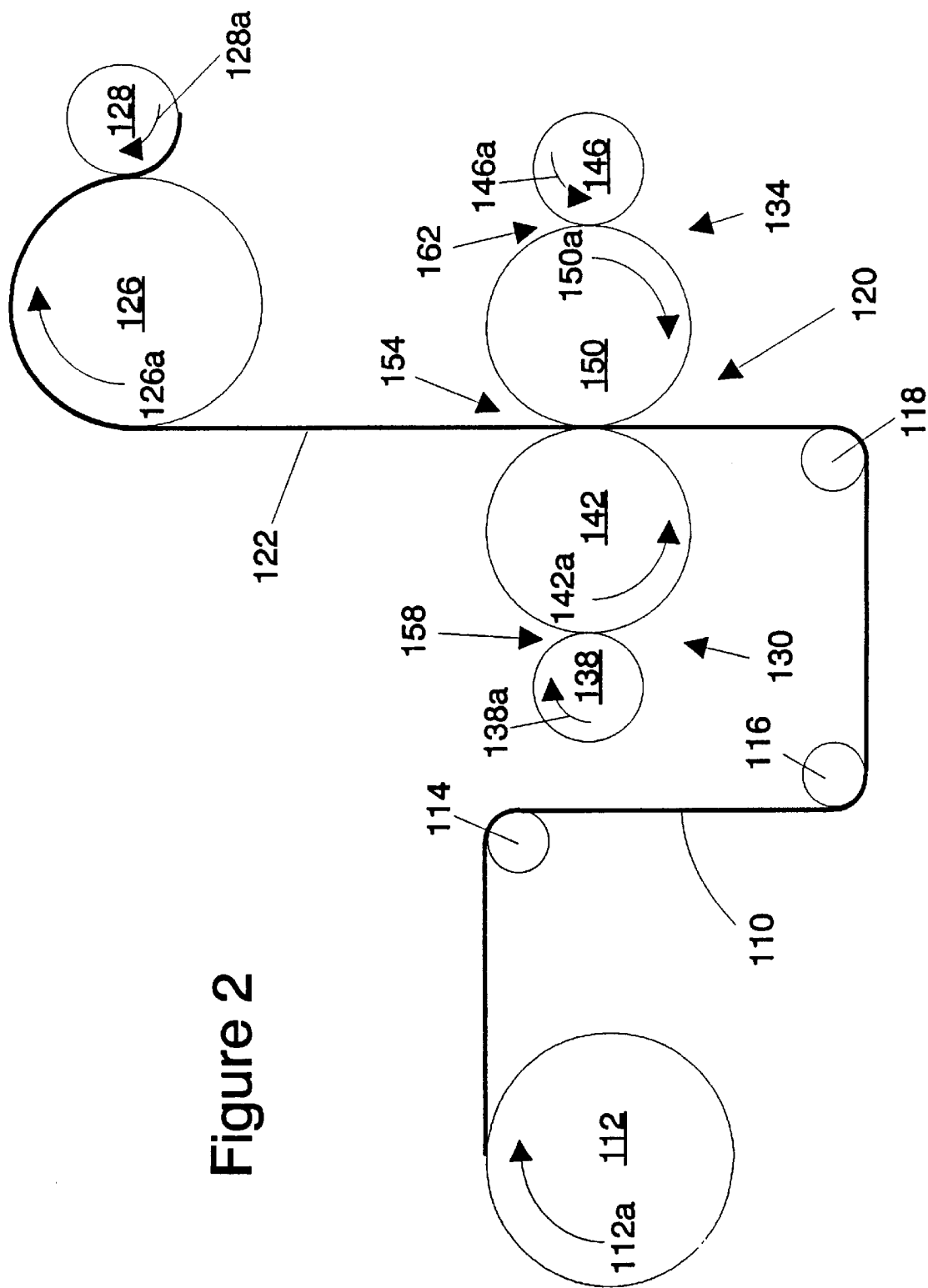
FIG. 2 is a schematic representation illustrating a system for applying the high internal phase inverse emulsions of the present invention by rotogravure coating to a carrier substrate such as a paper web.

FIG. 2 illustrates an alternative method for applying the high internal phase inverse emulsion involving a rotogravure coating system. Referring to FIG. 2, a dried paper web 110 is unwound from parent tissue roll 112 (rotating in the direction indicated by arrow 112a) and advanced around turning rolls 114, 116 and 118. From turning roll 118, web 110 is advanced to a gravure coating station indicated generally as 120 where the emulsion is then applied to both sides of the web. After leaving station 120, web 110 becomes a treated web indicated by 122. Treated web 122 is advanced to surface rewinder roll 126 (rotating in the direction indicated by arrow 126a) and then wound up on finished product roll 128 (rotating in the direction indicated by arrow 128a).

Station 120 comprises a pair of heated linked gravure presses 130 and 134. Press 130 consists of a smaller anilox cylinder 138 and a larger print plate cylinder 142; press 134 similarly consists of a smaller anilox cylinder 146 and a larger print plate cylinder 150. Anilox cylinders 138 and 146 each have a ceramic or chrome surface, while print plate cylinders 142 and 150 each have a relief patterned rubber, urethane, or photopolymer surface. These anilox and print plate cylinders rotate in the directions indicated by arrows 138a, 142a, 146a and 150a, respectively. As shown in FIG. 2, print plate cylinders 142 and 150 are opposed to one another and provide a nip area indicated by 154 through which web 110 passes.

Hot, molten (e.g., 60° C.) emulsion is pumped to or sprayed onto each of these linked gravure presses 130 and 134 at the nip areas indicated by arrows 158 and 162, respectively, at a constant volumetric flow rate. (Emulsion delivered to presses 130 and 134 may be the same or different.) In other words, the emulsion is added to the linked gravure presses 130 and 134 at the same rate as the emulsion is being applied to the web 110. This eliminates emulsion "build-up" in the system. As anilox cylinders 138 and 146 rotate in the directions indicated by arrows 138a and 146a, they act as rotating doctor blades to spread the emulsion evenly across the surfaces of print plate cylinders 142 and 150, respectively, and to remove excess emulsion from the print plates of cylinders 142 and 150.

The emulsion that is spread onto print plate cylinders 142 and 150 (rotating in the opposite direction as indicated by arrows 142a and 150b) is then transferred to both sides of web 110 at nip area 154. The amount of the emulsion transferred to web 110 can be controlled by: (1) adjusting the width of nip area 154 between print plate cylinders 142 and 150; (2) adjusting the width of nip areas 158 and 162 between anilox/print plate cylinder pairs 138/142 and 146/150; (3) the print image relief (i.e., valley depth) of the print plate on cylinders 142 and 150; (4) the print area (i.e., valley area) of the print plate on cylinders 142 and 150; and/or (6) the print pattern of the print plate on cylinders 142 and 150.

SPECIFIC ILLUSTRATIONS OF THE PREPARATION OF WET-LIKE CLEANING WIPES ACCORDING TO THE PRESENT INVENTION

The following are specific illustrations of the preparation of wet-like cleaning wipes in accordance with the present invention by treating tissue paper webs with high internal phase inverse emulsions:

EXAMPLE I

A) Emulsion Preparation

An emulsion is prepared from the following ingredients shown in Table I below:

TABLE I

| Ingredients | Amount (gm) | Percentage |
|---|---|---|
| Yellow Ceresine Wax (Strahl & Pitsch SP983) | 300 | 6% |
| Petrolatum (Fisher) | 100 | 2% |
| Sorbitan monoisostearate emulsifier (Crill ® 6 from Croda) | 200 | 4% |
| Sodium Chloride (EM Science) | 500 | 10% |
| Dantogard (preservative from Lonza) | 25 | 0.5% |
| Distilled Water | 3875 | 77.5% |

In formulating the internal phase component, the sodium chloride and Dantogard are added to the distilled water and then heated to 160° F. (71.1° C.). The remaining lipid phase ingredients (Yellow ceresine wax, petrolatum and Crill® 6) are heated, with mixing to a temperature of 170° F. (76.7° C.) until melted. The polar internal phase and lipid external phase components are then combined in a stainless steel vessel and mixed with a Hobart Model 100-C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Applying Emulsion to Substrate

The emulsion can be applied to a tissue paper web using the spray system shown in FIG. 1. The emulsion is heated to temperature of 60° C. so that it is fluid or molten. The ball screw drive 16 moves at linear velocity of 0.002 in/sec as it actuates piston 26 (3.5 in. diameter) to push the emulsion out of cylinder 22 (emulsion pressure at about 12 psig). The emulsion enters spray head 12 (external mixing spray head with spray setup SUE15 from Spray Systems Inc., Wheaton, Ill.) and is dispersed in air (at 1.2 psig) heated to about 60° C. The emulsion is then applied from head 12 as a dispersed spray to the web while the web is being rewound at about 28 ft/min. For example, the web can be sprayed at the nip between a rewinder roll and finished product (such as at the nip between surface rewinder roll 126 and finished parent roll 128 shown in FIG. 2). As a result, the emulsion coats both sides of the web at about 50% add-on.

The emulsion can also be applied to a tissue paper web substrate using the rotogravure coating system shown in FIG. 2. The hot, molten (e.g., 60° C.) emulsion is pumped to or sprayed onto each of these of linked gravure presses 130 and 134 at the nip areas indicated arrows by 158 and 162, respectively, at a constant volumetric flow rate of 20 ml/min. Anilox cylinders 138 and 146 spread the emulsion evenly across the surfaces of print plate cylinders 142 and 150, respectively (each rotating at about 40 feet/minute). Cylinders 142 and 150 then transfer the emulsion to both sides of web 110. The coated web 122 is transferred to surface rewinder roll 126 such that the coated central width of web 122 is over the depressed print area of roll 126. As a result, the coated central width of web 122 is not in contact with the surface of roll 126, while the noncoated edges of web 122 are in contact with the surface of roll 126. The web 122 is then wound up on finished product roll 128. The emulsion coats both sides of web 122 at about 50% add-on.

EXAMPLE II

A) Emulsion Preparation

An emulsion is prepared from the following ingredients are shown in Table II below:

TABLE II

| Ingredients | Amount (gm) | Percentage |
|---|---|---|
| Yellow Ceresine Wax (Strahl & Pitsch SP983) | 18 | 6% |
| Petrolatum (Fisher) | 3 | 1% |
| Sorbitan sesquioleate emulsifier (Arlacel ® 83 from ICI Specialties) | 12 | 4% |
| White Ozokerite Wax (Strahl & Pitsch SP1190) | 6 | 2% |
| 0.1% Pemulen TR1* in distilled water adjusted to pH 4.0 with NaOH | 261 | 87% |

*Pemulen TR1 is a hydrophobically modified acrylate thickener made by B.F Goodrich The lipid phase ingredients (yellow ceresine wax, petrolatum, white ozokerite wax and Arlacel 83) are heated and stirred in a 500 ml stainless steel beaker to a temperature of ~180° F. (82.8° C.) until melted. The internal polar phase component is prepared by adding 0.5 gin of Pemulen TR1 and 499.5 gm of distilled water to a 1 liter glass beaker, followed by mixing until the Pemulen TR1 is completely dissolved. The pH of this polar solution is adjusted to 4.0 with an appropriate amount of 1N NaOH. A portion (261 gm) of this polar solution is added to the beaker containing the lipid phase component. The combined mixture is heated to 160° F. (71.1° C.) and then mixed with a "Lightnin' TS2510" mixer at 500 rpm while allowing the ingredients to cool until the emulsion forms.

B) Applying Emulsion to Substrate

The emulsion is applied to a tissue paper web by either spraying or rotogravure coating according to the procedures of Example I.

EXAMPLE III

A) Emulsion Preparation

An emulsion is prepared from the following ingredients are shown in Table III below:

TABLE III

| Ingredients | Amount (gm) | Percentage |
|---|---|---|
| Yellow Ceresine Wax (Strahl & Pitsch SP983) | 18 | 6% |
| Sorbitan triooleate emulsifier (Span 85 ® from ICI Specialties) | 9 | 3% |
| Sodium Chloride | 21 | 7% |
| Distilled Water | 252 | 84% |

The lipid phase ingredients (yellow ceresine wax and Span® 85) are heated to ~160° F. (71.1° C.) and mixed in a 500 ml stainless steel beaker until melted. The remaining internal phase ingredients (sodium chloride and distilled water) are added to the beaker containing the lipid phase rents. The mixture is heated to 160° F. (71.1° C.) and then mixed using a "Lightnin' TS2510" mixer at 500 rpm. The mixture is allowed to cool until the emulsion forms.

B) Applying Emulsion to Substrate

The emulsion is applied to a tissue paper web by either spraying or rotogravure coating according to the procedures of Example I.

EXAMPLE IV

A) Emulsion Preparation

An emulsion is prepared from the following ingredients are shown in Table IV below:

TABLE IV

| Ingredients | Amount (gm) | Percentage |
|---|---|---|
| Paraffin wax (Aldrich) | 9 | 9% |
| Sorbitan monooleate emulsifier (Span 80 ® from ICI Specialties) | 3 | 3% |
| Calcium chloride dihydrate EM Science) | 4 | 4% |
| Distilled Water | 80 | 80% |

The lipid phase ingredients (paraffin wax and Span® 80) are heated to ~140° F. (60° C.) and mixed in a 500 ml stainless steel beaker until melted. The remaining internal phase ingredients (calcium chloride and distilled water) are added to the beaker containing the lipid phase ingredients. The mixture is heated to 140° F. (60° C.) and then mixed using a "Lightnin' TS2510" mixer at 500 rpm. The mixture is allowed to cool until the emulsion forms.

B) Applying Emulsion to Substrate

The emulsion is applied to a tissue paper web by either spraying or rotogravure coating according to the procedures of Example I.

EXAMPLE V

This example illustrates the preparation of an article comprising an emulsion applied to a paper substrate. The article is particularly suitable as a wipe for cleaning hard surface. The emulsion is added to either or both sides of the carrier (substrate).

A) Emulsion Preparation

An emulsion having 87% internal polar phase (consisting primarily of water) is prepared from the ingredients shown in Table V.

TABLE V

| Lipid Phase Ingredients: | Amount (gm) | Percentage |
|---|---|---|
| Strahl & Pitsch SP983 | 24 | 8.0 |
| Petrolatum | 6 | 2.0 |
| Sorbitan sesquioleate emulsifier (Arlacel ® 83 from ICI Specialties) | 9 | 3 |
| Polar Internal Phase Ingredients: | | |
| Distilled Water | 617.76 | 77.22 |
| HEDP | 0.16 | 0.02 |
| Hydrogen Peroxide | 5.6 | 0.7 |
| Ethanol | 69.6 | 8.7 |
| C-12 Amine Oxide | 0.8 | 0.10 |
| Geraniol | 1.04 | 0.13 |
| Limonene | 0.52 | 0.065 |
| Eukalyptol | 0.52 | 0.065 |

To formulate the polar phase, all components are mixed together and then heated to 140° F. (45.8° C.). Separately, the lipid phase ingredients are heated, with mixing, to a temperature of about 140° F. until melted. The polar and lipid phase components are then combined in a stainless steel vessel and mixed with a Hobart Model 100-C mixer on the low speed setting while allowing the ingredients to cool slowly. Mixing is continued until the water-in-lipid emulsion forms. Emulsion formation is evidenced by an increase in viscosity above 2000 centipoise as measured with a Lab-Line Instruments rotating disc viscometer.

B) Applying Emulsion to Carrier

The emulsion is applied to a tissue paper substrate by either spraying or rotogravure coating according to the procedures of Example I, or by screen printing. Emulsion may be added to either or both surfaces of the paper substrate.

EXAMPLE VI

A) Emulsion Preparation

A high internal phase emulsion (89% internal phase) is prepared from the ingredients shown in Table VI.

TABLE VI

| Ingredients | Amount (gm) | Percentage |
|---|---|---|
| Yellow Ceresine Wax (Strahl & Pitsch SP983) | 350 | 7% |
| Petrolatum (Fisher) | 50 | 1% |
| Sorbitan triooleate emulsifier (Span 85 ® from ICI Specialties) | 150 | 3% |
| Sodium Carbonate (anhydrous) | 25 | 0.5% |
| Dantogard (preservative from Lonza) | 25 | 0.5% |
| Denatured ethanol (3A from VRW Scientific) | 2000 | 40% |
| Distilled Water | 2400 | 48% |

In formulating the polar phase component, the Dantogard, sodium carbonate and ethanol are added to the distilled water and then heated to 160° F. (71.1° C.). Separately, the lipid phase ingredients (Yellow ceresine wax, petrolatum, and Span 85 emulsifier are heated, with mixing, to a temperature of about 170° F. (77° C.) until melted. The polar and lipid phase components are then combined in a stainless steel vessel and mixed with a Hobart Model 100 C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Applying Emulsion to Carrier

The emulsion is applied to a tissue paper substrate by either spraying or rotogravure coating according to the procedures of Example I, or by screen printing. Emulsion may be added to either or both surfaces of the paper substrate.

What is claimed is:

1. A process for applying an emulsion to a carrier, which comprises the steps of:
    A. forming at least one emulsion comprising:
        (1) from about 2 to about 60% of a continuous external lipid phase comprising a waxy lipid material having a melting point of about 40° C. or higher;
        (2) from about 39 to about 97% of an internal polar phase dispersed in the external lipid phase; and
        (3) an effective amount of an emulsifier capable of forming the emulsion when the external lipid phase is in a fluid state;
    B. applying said at least one emulsion to a carrier at a temperature sufficiently high such that the external lipid phase has a fluid or plastic consistency; and
    C. cooling the applied emulsion to a temperature sufficiently low such that the lipid external phase solidifies.

2. The process of claim 1 wherein the emulsion is applied to the carrier at a temperature in the range from about 60° to about 90° C.

3. The process of claim 2 wherein the emulsion is applied to the carrier at a temperature in the range from 70° to about 80° C.

4. The process of claim 1 wherein the emulsion is applied to the carrier by a step selected from the group consisting of spraying, printing, coating, extruding, and combinations thereof.

5. The process of claim 4 wherein the emulsion is applied to the carrier at a constant volumetric flow rate.

6. The process of claim 4 wherein the emulsion is applied to the carrier by a step selected from the group consisting of rotogravure coating and printing.

7. The process of claim 1 wherein the carrier is a paper web.

8. The process of claim 1 wherein the emulsion is applied to both sides of the carrier simultaneously.

9. The process of claim 1 wherein the carrier comprises two plies having opposed inner surfaces and wherein the emulsion is applied to at least one of the opposed inner surfaces.

10. The process of claim 1 wherein at least two different emulsions are applied to the carrier.

11. The process of claim 1 which comprises the further step of applying a detergent surfactant to the carrier separate from the emulsion, the detergent surfactant having an HLB value in the range of from about 10 to about 25.

12. The process of claim 1 wherein the emulsion comprises from about 5 to about 30% of the external lipid phase and from about 67 to about 92% of the internal polar phase.

13. The process of claim 12 wherein the waxy lipid material is selected from the group consisting of animal waxes, vegetable waxes, mineral waxes, synthetic waxes and mixtures thereof.

14. The process of claim 13 wherein the waxy lipid material is selected from the group consisting of beeswax, carnauba, spermaceti, lanolin, shellac wax, candelilla, paraffin, petrolatum, microcrystalline wax, white ceresine wax, yellow ceresine wax, white ozokerite wax, polyethylene waxes, chlorinated naphthalenes, and mixtures thereof.

15. The process of claim 14 wherein the waxy lipid material is selected from the group consisting of beeswax, lanolin, candelilla, petrolatum, microcrystalline wax, yellow ceresine wax, white ozokerite, polyethylene waxes, and mixtures thereof.

16. The process of claim 1 wherein the emulsifier comprises from about 1 to about 10% of the emulsion, and wherein the emulsifier has an HLB value in the range of from about 2 to about 5 and is selected from group consisting of sorbitan esters of $C_{16}$–$C_{22}$ saturated, unsaturated and branched chain fatty acids, glyceryl monoesters Of $C_{16}$–$C_{22}$ saturated, unsaturated and branched chain fatty acids, sucrose esters of $C_{12}$–$C_{22}$ saturated, unsaturated, and branched chain fatty acids, polyglycerol esters of $C_{16}$–$C_{22}$ saturated, unsaturated and branched chain fatty acids, and mixtures thereof.

17. The process of claim 16 wherein the emulsion comprises from about 5 to about 30% external lipid phase, from about 67 to about 92% internal polar phase, and from about 3 to about 6% emulsifier, and wherein the emulsifier is selected from group consisting of sorbitan monooleate, sorbitan monoisostearate, sorbitan sesquioleate, sorbitan stearates, sorbitan triooleate, sorbitan dipalmitates, glyceryl monosterate, glyceryl monopalmitate, glyceryl monobehenate, sucrose trilaurate, sucrose distearate, diglycerol monooleate, tetraglycerol monooleate, and mixtures thereof.

18. A process for applying an emulsion comprising an internal polar phase and an external lipid phase to a carrier, which comprises the steps of:
   A. forming at least one emulsion by combining at least the following materials:
      (1) from about 2 to about 60% of a waxy lipid material having a melting point of about 40° C. or higher;
      (2) from about 39 to about 97% of a polar material; and
      (3) an effective amount of an emulsifier capable of forming the emulsion when the lipid is in a fluid state;
      where the weight percent for each of components (1), (2) and (3) is determined from the amount of each component combined relative to the total weight of the emulsion;
   B. applying said at least one emulsion to a carrier at temperature sufficiently high such that the external lipid phase has a fluid or plastic consistency; and
   C. cooling the applied emulsion to a temperature sufficiently low such that the external lipid phase solidifies.

19. A process for applying an emulsion to a carrier, which comprises the steps of:
   A. forming at least one emulsion comprising:
      (1) from about 2 to about 15% of a continuous external lipid phase comprising a waxy lipid material having a melting point of about 30° C. or higher;
      (2) from about 82 to about 97% of an internal polar phase dispersed in the external lipid phase; and
      (3) an effective amount of an emulsifier capable of forming the emulsion when the external lipid phase is in a fluid state;
   B. applying said at least one emulsion to a carrier at a temperature sufficiently high such that the external lipid phase has a fluid or plastic consistency; and
   C. cooling the applied emulsion to a temperature sufficiently low such that the lipid external phase solidifies.

20. A process for applying an emulsion to a paper web, which comprises the steps of:
   A. forming at least one emulsion comprising:
      (1) from about 2 to about 60% of a continuous external lipid phase comprising a waxy lipid material having a melting point of about 30° C. or higher;
      (2) from about 39 to about 97% of an internal polar phase dispersed in the external lipid phase; and
      (3) an effective amount of an emulsifier capable of forming the emulsion when the external lipid phase is in a fluid state;
   B. applying said at least one emulsion to the paper web at a temperature sufficiently high such that the external lipid phase has a fluid or plastic consistency; and
   C. cooling the applied emulsion to a temperature sufficiently low such that the lipid external phase solidifies.

* * * * *

UNITED STATES PATENT AND TRADEMARK OFFICE
CERTIFICATE OF CORRECTION

PATENT NO. : 5,952,043  
DATED : September 14, 1999  
INVENTOR(S) : Larry N. Mackey et al.

Page 1 of 1

It is certified that error appears in the above-identified patent and that said Letters Patent is hereby corrected as shown below:

Column 2,  
Line 30, "pail" should read -- painful --.

Column 5,  
Line 53, "substrate" should read -- substrates --.  
Line 66, "type" should read -- types --.

Column 6,  
Line 28, "Cyananid" should read -- Cyanamid --.

Column 8,  
Line 45, "steiaryl" should read -- stearyl --.

Column 10,  
Line 60, "monosterate" should read -- monostearate --.

Column 13,  
Line 20, "surf" should read -- surface --.

Column 20,  
Line 2, "monosterate" should read -- monostearate --.

Signed and Sealed this

Twenty-sixth Day of February, 2002

Attest:

JAMES E. ROGAN  
*Attesting Officer*     *Director of the United States Patent and Trademark Office*